US012680943B2

(12) United States Patent
Enoki et al.

(10) Patent No.: US 12,680,943 B2
(45) Date of Patent: Jul. 14, 2026

(54) SNOW ENVIRONMENT TEST APPARATUS AND SNOW ENVIRONMENT TEST METHOD

(71) Applicant: ESPEC CORP., Osaka (JP)

(72) Inventors: Hiroyuki Enoki, Osaka (JP); Haruki Seto, Osaka (JP); Hemant Subhas Ningaraddi, Osaka (JP)

(73) Assignee: ESPEC CORP., Osaka (JP)

( * ) Notice: Subject to any disclaimer, the term of this patent is extended or adjusted under 35 U.S.C. 154(b) by 287 days.

(21) Appl. No.: 18/457,936

(22) Filed: Aug. 29, 2023

(65) Prior Publication Data

US 2024/0068930 A1     Feb. 29, 2024

(30) Foreign Application Priority Data

Aug. 30, 2022     (JP) ................................. 2022-137110

(51) Int. Cl.
G01N 17/00          (2006.01)
F25C 3/04           (2006.01)
(Continued)

(52) U.S. Cl.
CPC ............. G01N 17/002 (2013.01); F25C 3/04 (2013.01); G01N 17/00 (2013.01); G01N 33/00 (2013.01);
(Continued)

(58) Field of Classification Search
CPC ...... G01N 17/002; G01N 17/00; G01N 33/00; F25C 3/04; F25C 2303/0481; G01W 1/00; B01L 1/025
See application file for complete search history.

(56) References Cited

U.S. PATENT DOCUMENTS

| | | | | |
|---|---|---|---|---|
| 4,214,700 A | * | 7/1980 | Vanderkelen | F25C 3/04 |
| | | | | 239/14.2 |
| 2004/0261438 A1 | * | 12/2004 | Clulow | F25C 3/04 |
| | | | | 62/235 |
| 2022/0090837 A1 | | 3/2022 | Enoki et al. | |

FOREIGN PATENT DOCUMENTS

| | | | |
|---|---|---|---|
| DE | 102020107425 A1 | 10/2020 | |
| JP | S56-17548 U | 2/1981 | |
(Continued)

OTHER PUBLICATIONS

Kojima, S.; "Artificial snow used in environmental test facilities and its example of engineering applications"; Journal of the Japanese Society of Snow and Ice; Sep. 2018; total 10 pages; vol. 80, No. 5; DOI: 10.5331/seppyo.80.5_451.
(Continued)

*Primary Examiner* — Benjamin R Schmitt
(74) *Attorney, Agent, or Firm* — Studebaker Brackett PLLC

(57)          ABSTRACT

A snow environment test apparatus includes an injector including a two-fluid nozzle, a temperature setting section for setting an indoor temperature, an air conditioner for cooling an inside of a test chamber, a temperature control section for controlling the air conditioner, a water flow rate setting section for setting a flow rate of water to be supplied to the injector, and a snow quality selector for selecting snow quality. A related information storage section stores information in which a temperature in the test chamber, a flow rate of water to be supplied to the injector, a pressure of air to be supplied to the injector, and a snow quality are related with each other. A pressure regulator regulates the pressure of the air to be supplied to the injector to a pressure obtained by using the information stored in the related information storage section.

6 Claims, 12 Drawing Sheets

(51) Int. Cl.

| | | |
|---|---|---|
| *G01N 33/00* | (2006.01) | |
| *G05D 7/06* | (2006.01) | |
| *G05D 23/19* | (2006.01) | |
| *B01L 1/02* | (2006.01) | |
| *G01W 1/00* | (2006.01) | |

(52) U.S. Cl.

CPC ........... *G05D 7/0635* (2013.01); *G05D 23/19* (2013.01); *B01L 1/025* (2013.01); *F25C 2303/0481* (2013.01); *G01W 1/00* (2013.01)

(56) References Cited

FOREIGN PATENT DOCUMENTS

| | | | | | |
|---|---|---|---|---|---|
| JP | H02-136662 | A | | 5/1990 | |
| JP | H06-034244 | A | | 2/1994 | |
| JP | H07-055307 | A | | 3/1995 | |
| JP | 2020134261 | A | * | 8/2020 | ............. B01L 1/025 |
| WO | 99/017067 | A1 | | 4/1999 | |

OTHER PUBLICATIONS

"Notice of Reasons for Refusal" Office Action issued in JP 2022-137110; mailed by the Japanese Patent Office on Apr. 1, 2025.

Wei Zhao et al., "Design and Preliminary Experiment of Snow making Environment Simulator", Proceedings of the SPIE, SPIE, US, vol. 12080, Nov. 29, 2021.

The extended European search report issued by the European Patent Office on Jan. 29, 2024, which corresponds to European Patent Application No. 23193226.0-1001 and is related to U.S. Appl. No. 18/457,936.

* cited by examiner

START

SET TEMPERATURE IN TEST CHAMBER — ST11

SET TEST TIME — ST12

SET FLOW RATE OF WATER — ST13

SELECT SNOW QUALITY — ST14

CONTROL AIR CONDITIONER — ST15

START FIRST TEST — ST16

DERIVE AIR PRESSURE — ST17

REGULATE AIR PRESSURE — ST18

SECOND TEST — ST19

DERIVE AIR PRESSURE — ST20

REGULATE AIR PRESSURE — ST21

THIRD TEST — ST22

DERIVE AIR PRESSURE — ST23

REGULATE AIR PRESSURE — ST24

DERIVE
WATER TEMPERATURE — ST31

REGULATE
WATER TEMPERATURE — ST32

30

TEMPERATURE
SETTING SECTION — 30a

WATER FLOW RATE
SETTING SECTION — 30b

TEST TIME
SETTING SECTION — 30c

SNOW QUALITY
SELECTION SECTION — 30d

TEMPERATURE
CONTROL SECTION — 30e

RELATED INFORMATION
STORAGE SECTION — 30f

PRESSURE
CONTROL SECTION — 30g

WATER TEMPERATURE
CONTROL SECTION — 30h

DERIVE
AIR TEMPERATURE — ST41

REGULATE
AIR TEMPERATURE — ST42

SNOW ENVIRONMENT TEST APPARATUS AND SNOW ENVIRONMENT TEST METHOD

FIELD OF INVENTION

The present invention relates to a snow environment test apparatus and a snow environment test method.

BACKGROUND ART

Conventionally, JP S56-17548 U discloses a known snow environment test apparatus that reproduces a snow environment in a test chamber. In this snow environment test apparatus, a two-fluid nozzle that injects water and air is used. Since the two-fluid nozzle can inject fine water droplets, the snow environment test apparatus using the two-fluid nozzle can make powder snow.

In order to reproduce a snow environment, it is necessary to adjust the inside of the test chamber to a temperature environment of 0° C. or lower, but the snow quality is affected by the temperature in the test chamber and the like. Thus, in order to obtain desired snow quality, it is necessary to actually cause a certain amount of snow to fall in the test chamber, and to perform adjustment such as changing the temperature in the test chamber while checking the snow quality. Therefore, it takes time and effort for adjusting conditions to reproduce a snow environment where snow having desired snow quality is caused to fall.

SUMMARY OF THE INVENTION

An object of the present invention is to reduce time and effort for reproducing a snow environment where snow having desired snow quality is caused to fall.

A snow environment test apparatus according to one aspect of the present invention is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a water supply section configured to supply water having a predetermined temperature and the flow rate set by the water flow rate setting section to the injector, a snow quality selection section configured to select snow quality, a related information storage section storing information in which a temperature in the test chamber, a flow rate of water to be supplied to the injector, a pressure of air to be supplied to the injector, and a snow quality are related with each other, and a pressure regulation section configured to regulate the pressure of the air to be supplied to the injector to a pressure obtained by using the information stored in the related information storage section so that the snow quality selected by the snow quality selection section is obtained.

Further, a snow environment test apparatus according to another aspect of the present invention is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a water supply section configured to supply water having the flow rate set by the water flow rate setting section, an air supply section configured to supply air having a predetermined pressure to the injector, a snow quality selection section configured to select snow quality, a related information storage section storing information in which a temperature in the test chamber, a flow rate of water to be supplied to the injector, a temperature of water to be supplied to the injector, and a snow quality are related with each other, and a water temperature regulation section configured to regulate the temperature of the water to be supplied to the injector to a temperature obtained by using the information stored in the related information storage section so that the snow quality selected by the snow quality selection section is obtained.

Further, a snow environment test apparatus according to another aspect of the present invention is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a snow quality selection section configured to select snow quality, a related information storage section storing information in which a temperature in the test chamber, a flow rate of water to be supplied to the injector, a temperature of water to be supplied to the injector, a pressure of air to be supplied to the injector, and a snow quality are related with each other, a pressure regulation section configured to regulate the pressure of the air to be supplied to the injector to a pressure obtained by using the information stored in the related information storage section so that the snow quality selected by the snow quality selection section is obtained, and a water temperature regulation section configured to regulate the temperature of the water to be supplied to the injector to a temperature obtained by using the information stored in the related information storage section so that the snow quality selected by the snow quality selection section is obtained.

Further, a snow environment test apparatus according to another aspect of the present invention is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a water supply section configured to supply water having the flow rate set by the water flow rate setting section, an air supply section configured to supply air having a predetermined pressure to the injector, a snow quality selection section configured to select snow quality, a related information storage section storing information in which a temperature in the test chamber, a flow rate of water to be supplied to the injector, a temperature of air to be supplied to the injector, and a snow quality are related with each other, and an air temperature regulation section configured to regulate the temperature of the air to be supplied to the injector to a temperature obtained by using the information stored in the related information storage section so that the snow quality selected by the snow quality selection section is obtained.

Further, a snow environment test method according to another aspect of the present invention is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a pressure of air to be supplied to the injector providing the selected snow quality using information in which a temperature in the test chamber, a flow rate of water to be supplied to the injector, a pressure of air to be supplied to the injector, and a snow quality are related with each other, the information being stored in a related information storage section; supplying water having a predetermined temperature and the flow rate set by the water flow rate setting section to the injector; supplying air having the derived pressure to the injector; and injecting the water and the air from the injector.

Further, a snow environment test method according to another aspect of the present invention is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a temperature of the water to be supplied to the injector providing the selected snow quality using information in which a temperature in the test chamber, a flow rate of water to be supplied to the injector, a temperature of water to be supplied to the injector, and a snow quality are related with each other, the information being stored in a related information storage section; supplying water, having the derived temperature and the flow rate set by the water flow rate setting section, to the injector; supplying air having a predetermined pressure to the injector; and injecting the water and the air from the injector.

Further, a snow environment test method according to another aspect of the present invention is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a pressure of air to be supplied to the injector providing the selected snow quality and deriving a temperature of the water to be supplied to the injector providing the selected snow quality, using information in which a temperature in the test chamber, a flow rate of water to be supplied to the injector, a temperature of water to be supplied to the injector, a pressure of air to be supplied to the injector, and a snow quality are related with each other, the information being stored in a related information storage section; supplying water having the derived temperature and the flow rate set by the water flow rate setting section to the injector; supplying air having the derived pressure to the injector; and injecting the water and the air from the injector.

Further, a snow environment test method according to another aspect of the present invention is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a temperature of air to be supplied to the injector providing the selected snow quality using information in which a temperature in the test chamber, a flow rate of water to be supplied to the injector, a temperature of air to be supplied to the injector, and a snow quality are related with each other, the information being stored in a related information storage section; supplying water having a predetermined temperature and the flow rate set by the water flow rate setting section to the injector; supplying air having a predetermined pressure and the derived temperature to the injector; and injecting the water and the air from the injector.

DETAILED DESCRIPTION

Embodiments for carrying out the present invention will be described in detail below with reference to the drawings.

First Embodiment

Figure 1:
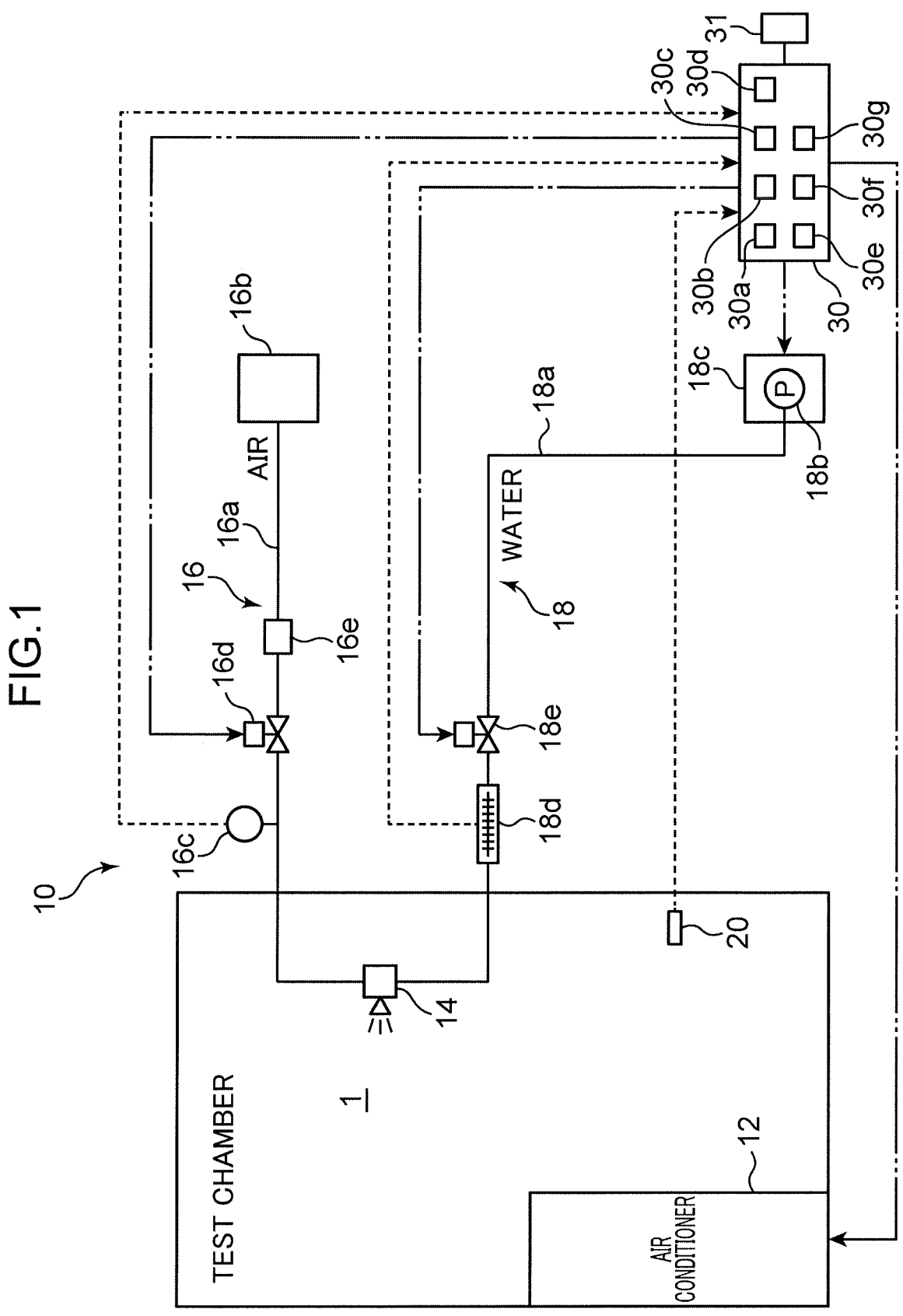
FIG. 1 is a diagram schematically illustrating a snow environment test apparatus according to a first embodiment.

As illustrated in FIG. 1, a snow environment test apparatus 10 according to a first embodiment is an apparatus that creates a snow environment of desired snow quality in a test chamber 1 and performs a test for exposing a specimen disposed in the test chamber 1 to the snow environment. Here, the snow quality means a property of snow or the like indicating dry snow, wet snow, or sleet. Since the snow environment test apparatus 10 of the present embodiment can also create a rain environment in addition to the snow environment having desired snow quality, the snow quality referred to in the first embodiment includes rain. The snow quality may include properties of snow and the like, such as water content. The snow environment test apparatus 10 according to the present embodiment can create not only a snow environment that causes snow to fall, but also a snow environment that causes sleet containing snow and rain in a mixed manner to fall. Furthermore, the snow environment test apparatus 10 of the present embodiment is configured to be able to create not only these snow environments but also the rain environment.

The snow environment test apparatus 10 includes an air conditioner 12 for cooling the inside of the test chamber 1, an injector 14 configured to inject air and water into the test chamber 1, an air supply section 16 for supplying air to the injector 14, and a water supply section 18 for supplying water to the injector 14.

The air conditioner 12 is configured to generate low-temperature air so as to be able to cool the air in the test chamber 1. The air conditioner 12 is caused to be able to adjust the temperature in the test chamber 1 to a predetermined temperature of at least less than 0° C. That is, the air conditioner 12 adjusts the temperature of the air in the test chamber 1 so that fine water droplets injected from the injector 14 have a freezing temperature. The air conditioner 12 can adjust the temperature in the test chamber 1 within a range between, for example, 0° C. and −30° C. Note that when the rain environment is created, the air conditioner 12 may adjust the temperature in the test chamber 1 to a temperature higher than 0° C., for example, a temperature between 0° C. and 20° C.

The temperature in the test chamber 1 is detected by a room temperature sensor 20.

The injector 14 is configured by a two-fluid nozzle (spray nozzle), and is configured to be able to inject a fluid in a state where fine water droplets (fine water particles) and air are mixed. That is, the two-fluid nozzle injects the water supplied from the water supply section 18 and the air supplied from the air supply section 16 together while dispersing the water. At this time, since the injected water is pulverized by the injected air, fine water droplets (fine water particles) and air are injected from the two-fluid nozzle. Therefore, the injector 14 can inject finer water droplets as the pressure of air to be supplied increases.

The air supply section 16 includes an air pipe 16a connected to the injector 14 and a compressor 16b that causes air to flow towards the injector 14 in the air pipe 16a. The air pipe 16a is provided with a pressure sensor 16c for detecting the pressure of air flowing through the air pipe 16a, and a pressure regulation valve 16d for regulating the pressure of the air flowing through the air pipe 16a. The pressure regulation valve 16d regulates the pressure of the air flowing through the air pipe 16a. This regulates the pressure of the air introduced into the injector 14. The air pipe 16a is provided with a heating and cooling unit (air temperature regulator) 16e for heating or cooling the air flowing through the air pipe 16a. The heating and cooling unit 16e may be driven so as to keep the temperature of the air introduced into the injector 14 constant, and in this case, can prevent snow quality from being varied by the air to be supplied to the injector 14. Note that the heating and cooling unit 16e can be omitted.

The water supply section 18 includes a water pipe 18a connected to the injector 14 and a pump 18b that causes water to flow towards the injector 14 in the water pipe 18a. The water pipe 18a is provided with a heating and cooling unit 18c. Water heated or cooled by the heating and cooling unit 18c (water temperature regulator) to a predetermined temperature is introduced into the injector 14. The water pipe 18a is further provided with a flowmeter 18d for detecting the flow rate of the water flowing through the water pipe 18a, and a flow rate regulation valve 18e for regulating the flow rate of the water flowing through the water pipe 18a. The flow rate regulation valve 18e adjusts the flow rate of the water flowing through the water pipe 18a. This regulates the flow rate of the water introduced into the injector 14. Note that the heating and cooling unit 18c may or may not be electrically connected to a controller 30 described later. The heating and cooling unit 18c is disposed to maintain the temperature of the water to be supplied to the injector 14 at a predetermined temperature. Note that if the temperature of water discharged from the pump 18b is stable, the heating and cooling unit 18c can be omitted.

Figure 2:
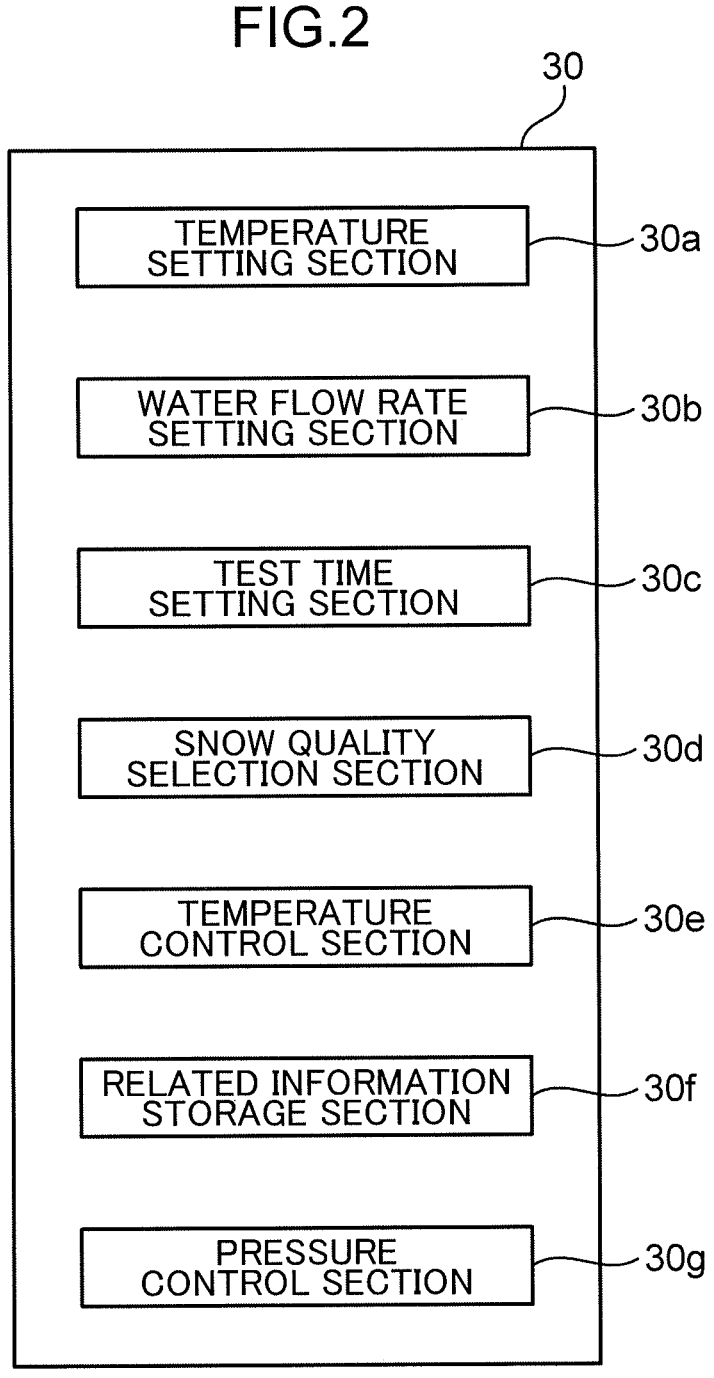
FIG. 2 is a diagram for describing functions of a controller.

The room temperature sensor 20, the pressure sensor 16c, the pressure regulation valve 16d, the heating and cooling unit 18c, the flowmeter 18d, and the flow rate regulation valve 18e are connected to the controller 30 so as to be able to transmit and receive signals. The controller 30 is a computer for controlling various operations of the snow environment test apparatus 10, and includes a microcomputer having a central processing unit (CPU) that executes arithmetic processing, a read only memory (ROM) that stores a processing program, data, and the like, and a random access memory (RAM) that temporarily stores data. An input device 31 is connected to the controller 30. By executing the processing program stored in the controller 30, as illustrated in FIG. 2, the controller 30 can be caused to function as a temperature setting section 30a, a water flow rate setting section 30b, a test time setting section 30c, a snow quality selection section 30d, a temperature control section 30e, a related information storage section 30f, and a pressure control section 30g.

The temperature setting section 30a is a functional unit for setting the temperature (test temperature) in the test chamber 1. For example, when a tester inputs a temperature through the input device 31, information indicating the input temperature is stored.

The temperature control section 30e is configured to cause the air conditioner 12 to make the temperature detected by the room temperature sensor 20 be the temperature set by the temperature setting section 30a.

The water flow rate setting section 30b is a functional unit for setting the flow rate of water to be supplied to the injector 14. For example, when the tester inputs a flow rate of the water through the input device 31, information indicating the input flow rate of the water is stored.

The test time setting section 30c is a functional unit for setting a test time during which a created snow environment is continued. For example, when the tester inputs a test time through the input device 31, information indicating the input test time is stored.

The snow quality selection section 30d is a functional unit for selecting snow quality among prepared options, and is configured to be able to select any one of dry snow, wet snow, sleet, and rain as prepared options. The snow quality selection section 30d may be configured to be able to select or set the degree of sleet or the water content. Dry snow, wet snow, sleet, or rain is selected through the input device 31. When the tester selects dry snow, for example, through the input device 31, information indicating that dry snow has been selected is stored in the snow quality selection section 30*d*. In addition, the snow quality selection section 30*d* may be configured to be able to select only one of dry snow, wet snow, sleet, and rain, but in the present embodiment, is supposed to be configured to be able to select a plurality of them. That is, in a case where a plurality of types of snow is selected from dry snow, wet snow, sleet, and rain, it is also possible to perform a test of forming any selected snow environment (or rain environment) and then changing the selected snow environment to another selected snow environment (or rain environment). For example, dry snow can be selected for the first test, and wet snow can be selected for the second test. In this case, the snow environment test apparatus 10 first causes dry snow to fall for a predetermined time, and then performs a control operation for causing wet snow to fall for a predetermined time.

Note that the snow quality prepared as options is not limited to dry snow, wet snow, sleet, and rain. For example, snow and sleet may be prepared as options while rain may be excluded, or only dry snow and wet snow may be provided as options.

Figure 3:
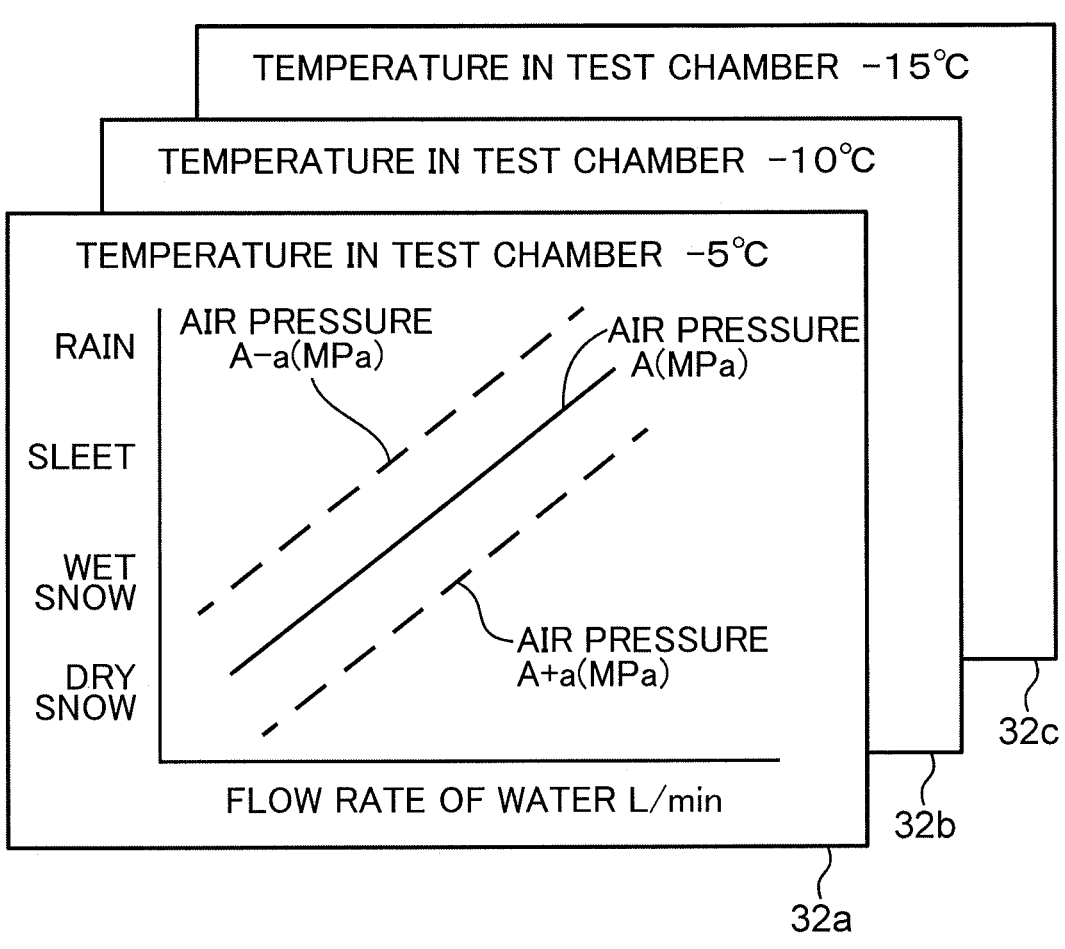
FIG. 3 is a diagram for describing information stored in a related information storage section.

The related information storage section 30*f* is a functional unit that stores information in which the temperature in the test chamber 1, the flow rate of the water to be supplied to the injector 14, the pressure of air to be supplied to the injector 14, and the snow quality (however, rain is also included in the present embodiment) are related with each other. As illustrated in FIG. 3, the related information storage section 30*f* may include, for example, a first map 32*a*, a second map 32*b*, and a third map 32*c*. In the first map 32*a*, the flow rate of water, the air pressure, and the snow quality at a first test temperature (for example, −5° C.) are related with each other. In the second map 32*b*, the flow rate of water, the air pressure, and the snow quality at a second test temperature (for example, −10° C.) are related with each other. In the third map 32*c*, the flow rate of water, the air pressure, and the snow quality at a third test temperature (for example, −15° C.) are related with each other. That is, use of the stored information makes it possible to derive which snow quality is obtained in a case of a certain air pressure and a certain flow rate of water at each test temperature. In addition, in a case where certain snow quality is desired to be obtained at each test temperature, it is possible to derive how much air pressure (MPa) may be set under a certain flow rate of water. The information stored in the first to third maps 32*a* to 32*c* can be obtained by a preliminary test to cause snow to fall after regulating of the test chamber temperature, the flow rate of water, and the air pressure are regulated, and then to check actual snow quality.

Note that as the snow quality, dry snow, wet snow, sleet, and rain are stored as options, but instead of or together with them, the degree of sleet or the water content may be stored. Further, the information stored in the related information storage section 30*f* may be information expressed by a relational expression, information in the form of a list, or the like. In addition, the number of prepared test temperatures is not limited to three, and information in the case of one, two, or more test temperatures may be prepared. In a case where information related to a plurality of test temperatures is stored, the controller 30 may function as a temperature interpolation control section that creates a map of a new test temperature by interpolation such as linear interpolation.

The new test temperature corresponds to the temperature in the test chamber 1 set by the temperature setting section 30*a*.

The pressure control section 30*g* is configured to derive the pressure of the air to be supplied to the injector 14 using the temperature in the test chamber 1 set in the temperature setting section 30*a*, the flow rate of the water set in the water flow rate setting section 30*b*, the snow quality set in the snow quality selection section 30*d*, and the information stored in the related information storage section 30*f*. For example, in a case where the information illustrated in FIG. 3 is stored in the related information storage section 30*f*, the pressure control section 30*g* refers to a map of a test temperature matching or similar to the temperature in the test chamber 1 set in the temperature setting section 30*a*. In the referred map, the air pressure corresponding to the flow rate of water set in the water flow rate setting section 30*b* and the snow quality set in the snow quality selection section 30*d* is derived. The pressure control section 30*g* is configured to control the pressure regulation valve 16*d* to make the pressure of the air to be supplied to the injector 14 become the air pressure that is derived by using the temperature in the test chamber 1 set in the temperature setting section 30*a*, the flow rate of water set in the water flow rate setting section 30*b*, the snow quality set in the snow quality selection section 30*d*, and the information stored in the related information storage section 30*f*. That is, the pressure control section 30*g* and the pressure regulation valve 16*d* function as a pressure regulation section that regulates the pressure of the air to be supplied to the injector 14 to the pressure obtained by using the information stored in the related information storage section 30*f*.

Figure 4:
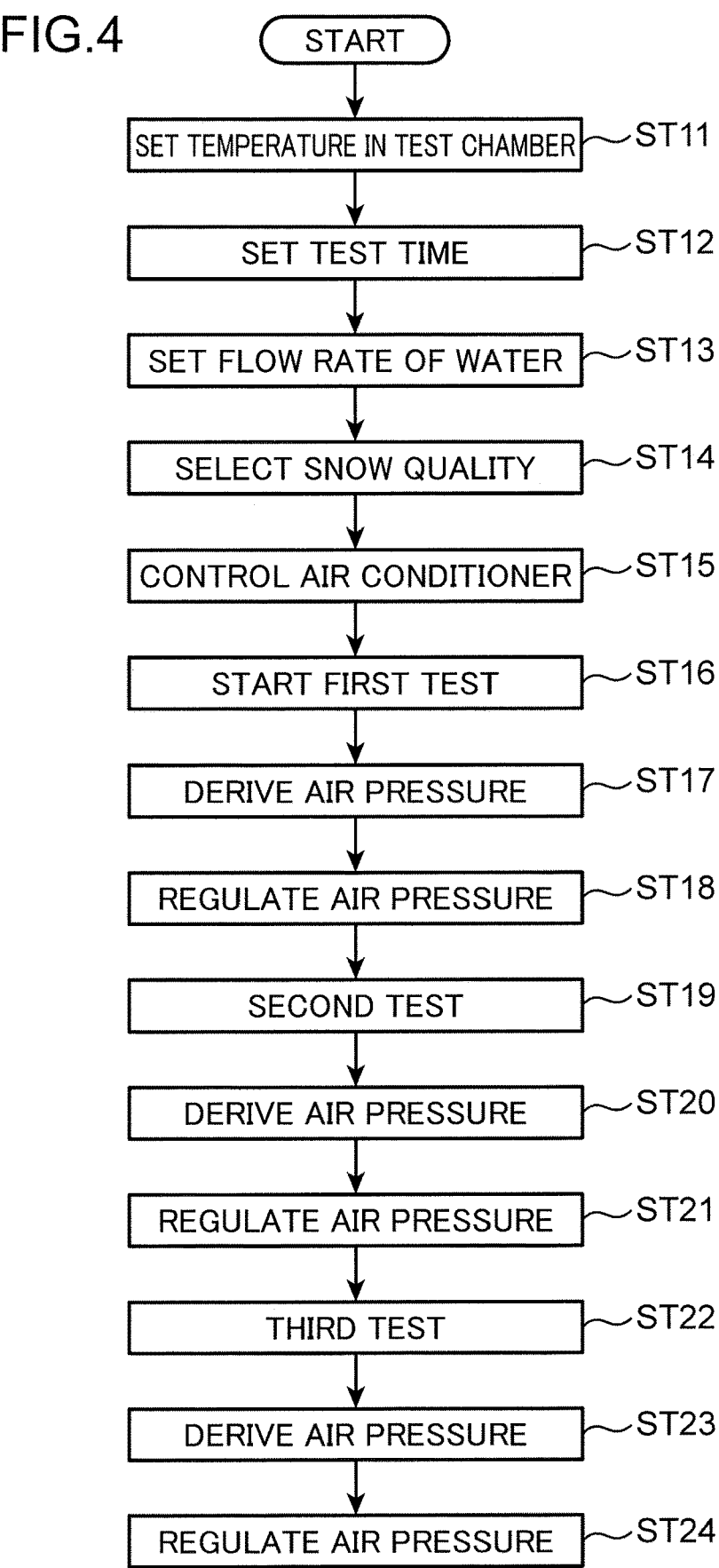
FIG. 4 is a flowchart for describing a snow environment test method according to the first embodiment.
Figure 5:
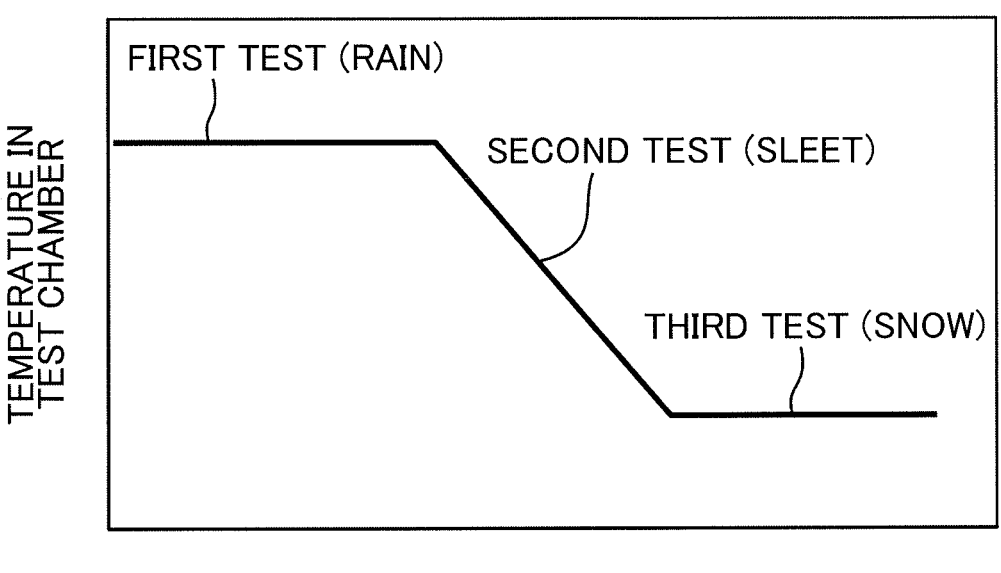
FIG. 5 is a diagram for describing an example of the snow environment test method according to the first embodiment.

Here, a method for performing a snow environment test using the snow environment test apparatus 10 will be described with reference to FIG. 4. Note that as an example of the test method, a case where the test is performed in the order of rainfall (first test), sleet (second test), and wet snow (third test) as illustrated in FIG. 5 will be described. Note that since the injector 14 is configured by the two-fluid nozzle, in a case where the rainfall test is performed, rain is drizzle whose water droplets are very fine.

In the snow environment test method, a test specimen is first disposed in the test chamber 1, and then a tester inputs a test temperature and a test time through the input device 31. At this time, the tester inputs the test temperature and the test time for each of the first test, the second test, and the third test. As a result, the test temperature is set in the temperature setting section 30*a*, and the test time is set in the test time setting section 30*c* (steps ST11 and ST12).

In addition, the tester inputs the flow rate of the water to be injected from the injector 14 through the input device 31. At this time, the tester inputs the identical flow rate of the water in the first to third tests, for example. Thus, the flow rate of the water is set in the water flow rate setting section 30*b* (step ST13). Further, the tester selects snow quality through the input device 31. At this time, the tester selects, for example, rain for the first test, sleet for the second test, and wet snow for the third test. As a result, the snow quality is selected in the snow quality selection section 30*d* (step ST14). Note that the flow rate of the water may be constant in the first to third tests, or may be set to be higher or lower in the second and third tests than in the first test. The test temperature may be gradually reduced in the second test, but may be maintained at a constant temperature also in the second test.

Subsequently, the air conditioner 12 operates, and the temperature control section 30*e* causes the air conditioner 12 to make the temperature in the test chamber 1 detected by the room temperature sensor 20 be the temperature set in the temperature setting section 30*a* (step ST15). Then, when the temperature in the test chamber 1 reaches the set temperature, the test is started (step ST16). Thus, the test time is counted.

To start with the first test, the air conditioner 12 is caused to make the temperature in the test chamber 1 be the temperature set as the temperature of the first test. Further, the air supply section 16 supplies air to the injector 14 through the air pipe 16*a*, and the water supply section 18 supplies water to the injector 14 through the water pipe 18*a*. As a result, a fluid in which fine water droplets and air are mixed is injected from the injector 14.

During the test, the pressure control section 30*g* derives the pressure of the air to be supplied to the injector 14 using the temperature in the test chamber 1 set in the temperature setting section 30*a*, the flow rate of the water set in the water flow rate setting section 30*b*, the snow quality set in the snow quality selection section 30*d*, and the information stored in the related information storage section 30*f* (step ST17). That is, the pressure control section 30*g* derives the air pressure from the set temperature in the test chamber 1, the set flow rate of water, and the set snow quality (rain) using the information stored in the related information storage section 30*f*. The pressure control section 30*g* controls the pressure regulation valve 16*d* depending on the derived pressure. As a result, during the test, the pressure of the air to be supplied to the injector 14 is regulated to be the derived pressure (step ST18). On the other hand, the temperature of the water to be supplied to the injector 14 is regulated to a predetermined temperature by the heating and cooling unit 18*c*. The flow rate regulation valve 18*e* is caused to regulate the flow rate so that the flow rate measured by the flowmeter 18*d* becomes the flow rate of the water set in the water flow rate setting section 30*b*. This provides a rain environment corresponding to "rain" selected in the snow quality selection section 30*d*. In this state, the rainfall test is continued.

In this state, when the set test time has elapsed, the processing proceeds to the second test (step ST19). In the second test, the air conditioner 12 is controlled to make the temperature in the test chamber 1 become the temperature set for the second test. In addition, water having the set flow rate and the water temperature cooled by the heating and cooling unit 18*c* is supplied to the injector 14. Also in the second test, the pressure of the air to be supplied to the injector 14 is derived by using the set temperature in the test chamber 1, the set flow rate of the water, the set snow quality, and the information stored in the related information storage section 30*f* (step ST20). Further, the pressure regulation valve 16*d* is controlled depending on the derived pressure (step ST21). This provides a snow environment corresponding to "sleet" selected in the snow quality selection section 30*d*. In this state, the sleet test is continued.

In this state, when the set test time has elapsed, the processing proceeds to the third test (step ST22). In the third test, the air conditioner 12 is controlled to make the temperature in the test chamber 1 become the temperature set for the third test. In addition, water having the set flow rate and the water temperature cooled by the heating and cooling unit 18*c* is supplied to the injector 14. Also in the third test, the pressure of the air to be supplied to the injector 14 is derived by using the set temperature in the test chamber 1, the set flow rate of the water, the set snow quality, and the information stored in the related information storage section 30*f* (step ST23). Further, the pressure regulation valve 16*d* is controlled depending on the derived pressure (step ST24).

Specifically, the pressure of the air to be supplied to the injector 14 is regulated to increase so that the snow quality is changed from sleet of the second test to wet snow of the third test. This provides a snow environment corresponding to "wet snow" selected in the snow quality selection section 30*d*. In this state, the wet snow test is continued. Then, when the set time has elapsed, the third test ends.

As described above, in the present embodiment, the temperature control section 30*e* controls the air conditioner 12 to make the temperature in the test chamber 1 become the set temperature. The pressure regulation valve 16*d* regulates the pressure of the air to be supplied to the injector 14 to a pressure obtained by using the snow quality selected by the snow quality selection section 30*d* and the information stored in the related information storage section 30*f*. As a result, air having the regulated pressure is supplied to the injector 14, and the water having the flow rate set in water flow rate setting section 30*b* and a predetermined temperature is supplied to the injector 14. Therefore, the snow environment of the snow quality selected by the snow quality selection section 30*d* can be obtained, and the specimen can be exposed to such a snow environment. Moreover, since the snow quality is changed by regulating the pressure of the air to be supplied to the injector 14, the snow quality can be quickly changed. For example, at a shift from the second test for causing sleet to fall to the third test for causing wet snow to fall, the pressure of the air to be introduced into the injector 14 is regulated to become high, and this enables a smooth shift from sleet to wet snow.

In addition, the related information storage section 30*f* is provided to store information in which three conditions (the temperature in the test chamber 1, the flow rate of the water to be supplied to the injector 14, and the pressure of the air to be supplied to the injector 14) are related with the snow quality. By using the stored information, the pressure of the air to be supplied to the injector 14 is regulated depending on a predetermined temperature in the test chamber 1 and a predetermined water flow rate at a predetermined temperature. Thus, a snow environment of desired snow quality can be obtained. Therefore, the time and effort for obtaining desired snow quality can be reduced. Note that the information stored in the related information storage section 30*f* can be acquired by a preliminary test to cause snow to fall in the test chamber 1 after the regulating of these three conditions and check the snow quality.

Second Embodiment

Figure 6:
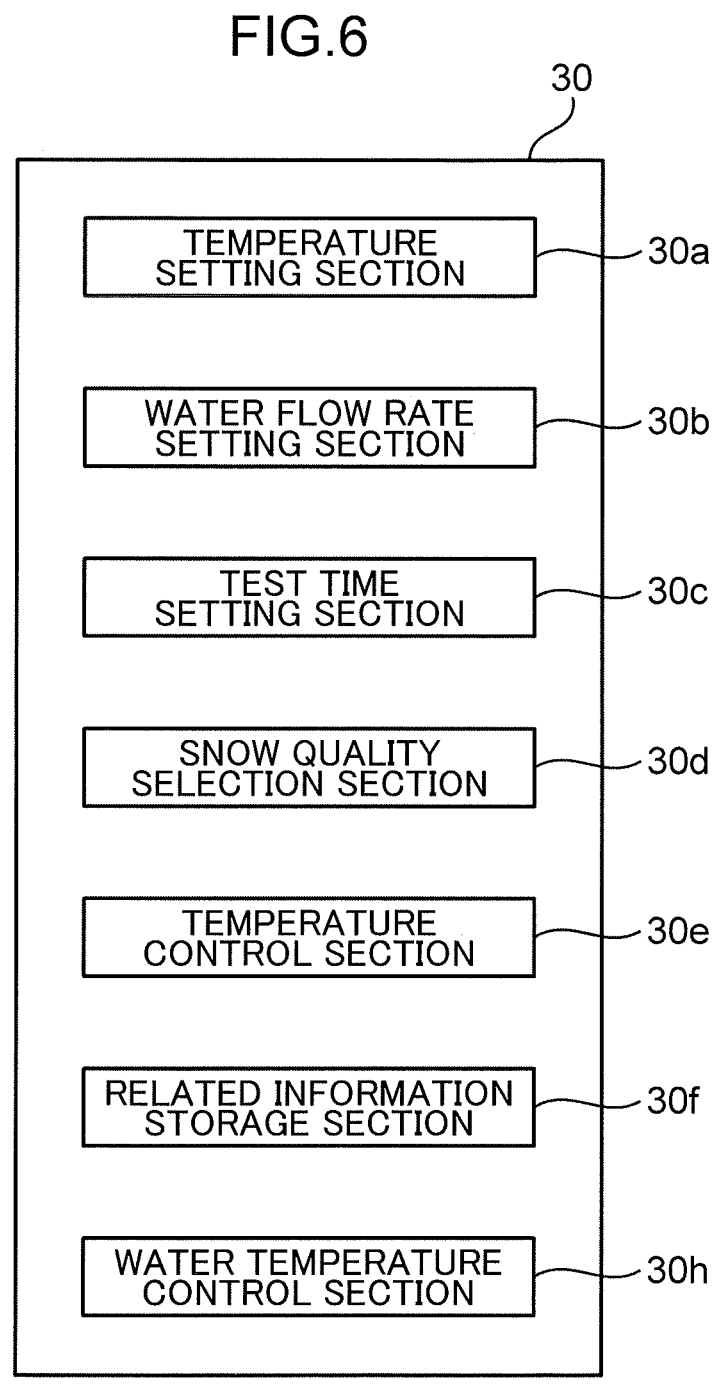
FIG. 6 is a diagram for describing functions of a controller in a snow environment test apparatus according to a second embodiment.

As illustrated in FIG. 6, in the second embodiment, the controller 30 also functions as a water temperature control section 30*h* in order to regulate the temperature of the water to be supplied to the injector 14 using the information stored in the related information storage section 30*f*. Note that the components identical to those in the first embodiment are denoted by the identical reference numerals, and the detailed description thereof will be omitted.

In the second embodiment, unlike the first embodiment, the pressure control section 30*g* is omitted. Therefore, although the pressure regulation valve 16*d* is provided to the air pipe 16*a*, the pressure regulation valve 16*d* may not be connected to the controller 30. The pressure regulation valve 16*d* is provided to maintain the pressure of the air to be supplied to the injector 14 at a predetermined pressure. However, if the pressure of the air to be discharged from the compressor 16*b* is stable, the pressure regulation valve 16*d* can be omitted.

Figure 7:
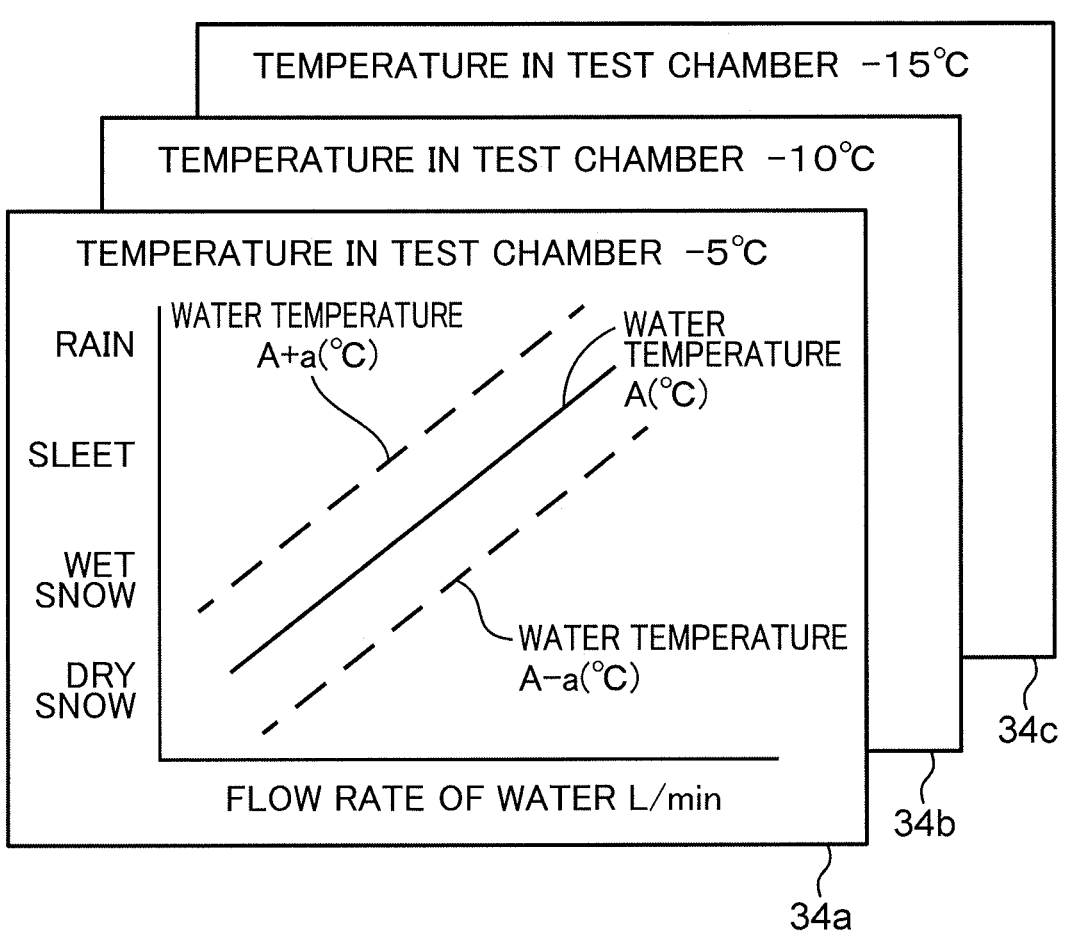
FIG. 7 is a diagram for describing information stored in a related information storage section.

The related information storage section 30*f* is a functional section that stores information in which the temperature in the test chamber 1, the flow rate of the water to be supplied to the injector 14, the temperature of the water to be supplied to the injector 14, and the snow quality are related with each other. As illustrated in FIG. 7, the related information storage section 30*f* may include, for example, a first map 34*a*, a second map 34*b*, and a third map 34*c*. In the first map 34*a*, the flow rate of water, the water temperature, and the snow quality at the first test temperature (for example, −5° C.) are related with each other. In the second map 34*b*, the flow rate of water, the water temperature, and the snow quality at the second test temperature (for example, −10° C.) are related with each other. In the third map 34*c*, the flow rate of water, the water temperature, and the snow quality at the third test temperature (for example, −15° C.) are related with each other. That is, use of the information stored in the related information storage section 30*f* makes it possible to derive which snow quality is obtained in the case of a certain water temperature and a certain flow rate of water at each test temperature. In addition, in a case where a certain snow quality is desired to be obtained at each test temperature, it is possible to derive what water temperature (° C.) may be set under a certain flow rate of water. Note that dry snow, wet snow, sleet, and rain are stored as the snow quality, but instead of or together with them, the degree of sleet or the water content may be stored. Further, the information stored in the related information storage section 30*f* may be information expressed by a relational expression, information in the form of a list, or the like. In addition, the number of prepared test temperatures is not limited to three, and information in the case of one, two, or more test temperatures may be prepared.

The water temperature control section 30*h* is configured to derive the temperature of the water to be supplied to the injector 14 using the temperature in the test chamber 1 set in the temperature setting section 30*a*, the flow rate of the water set in the water flow rate setting section 30*b*, the snow quality set in the snow quality selection section 30*d*, and the information stored in the related information storage section 30*f*. For example, in a case where the information illustrated in FIG. 7 is stored in the related information storage section 30*f*, the water temperature control section 30*h* refers to a map of a test temperature matching or similar to the temperature in the test chamber 1 set in the temperature setting section 30*a*. In the referred map, the water temperature is derived from the flow rate of water set in the water flow rate setting section 30*b* and the snow quality set in the snow quality selection section 30*d*. The water temperature control section 30*h* is configured to control the heating and cooling unit 18*c* to make the temperature of the water to be supplied to the injector 14 be the temperature that is derived by using the temperature in the test chamber 1 set in the temperature setting section 30*a*, the flow rate of the water set in the water flow rate setting section 30*b*, the snow quality set in the snow quality selection section 30*d*, and the information stored in the related information storage section 30*f*. That is, the water temperature control section 30*h* and the heating and cooling unit 18*c* function as a water temperature regulation section that regulates the temperature of the water to be supplied to the injector 14 to be the temperature obtained by using the information stored in the related information storage section 30*f*.

Figure 8:
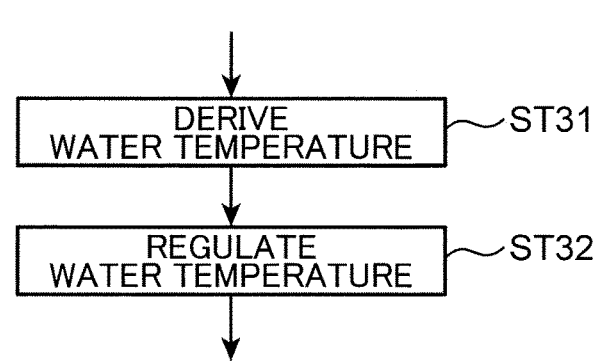
FIG. 8 is a flowchart for describing adjustment of a water temperature in a snow environment test method according to the second embodiment.

Here, as in the first embodiment, an example in the case where the test illustrated in FIG. 5 is performed will be described. In the second embodiment, as illustrated in FIG. 8, in each of the first to third tests, the water temperature control section 30*h* derives the temperature of the water to be supplied to the injector 14 using the temperature in the test chamber 1 set in the temperature setting section 30*a*, the flow rate of the water set in the water flow rate setting section 30*b*, the snow quality set in the snow quality selection section 30*d*, and the information stored in the related information storage section 30*f* (step ST31). In addition, the water temperature control section 30*h* controls the heating and cooling unit 18*c* depending on the derived temperature. As a result, during the test, the temperature of the water to be supplied to the injector 14 is regulated to be the derived temperature (step ST32). Specifically, the temperature of the water to be supplied to the injector 14 is regulated to decrease so that the snow quality is changed from sleet of the second test to wet snow of the third test. At this time, the flow rate of water is regulated to the flow rate of the water set in the water flow rate setting section 30*b*. On the other hand, the air to be supplied to the injector 14 is regulated by the pressure regulation valve 16*d* to be a predetermined pressure. That is, unlike the first embodiment, the second embodiment does not include the step of deriving the air pressure using the information stored in the related information storage section 30*f* (steps ST17, ST20, and ST23) and the step of regulating the air pressure using the information stored in the related information storage section 30*f* (ST18, ST21, and ST24).

Therefore, in the present embodiment, the temperature control section 30*e* controls the air conditioner 12 to make the temperature in the test chamber 1 be the set temperature. The heating and cooling unit 18*c* regulates the temperature of the water to be supplied to the injector 14 to a water temperature obtained by using the snow quality selected by the snow quality selection section 30*d* and the information stored in the related information storage section 30*f*. As a result, water having the regulated temperature and the flow rate set in the water flow rate setting section 30*b*, and air having a predetermined pressure are supplied to the injector 14. In such a manner, the snow environment of the snow quality selected by the snow quality selection section 30*d* can be obtained, and the specimen can be exposed to such a snow environment. In addition, in the configuration where the water temperature is regulated by using the information stored in the related information storage section 30*f*, as in the second embodiment, a regulation width of the snow quality can be made wider than in the configuration where the air pressure is regulated as in the first embodiment.

Note that although the descriptions of other configurations, operations, and effects are omitted, the description of the first embodiment can be applied to the second embodiment.

Third Embodiment

Figure 9:
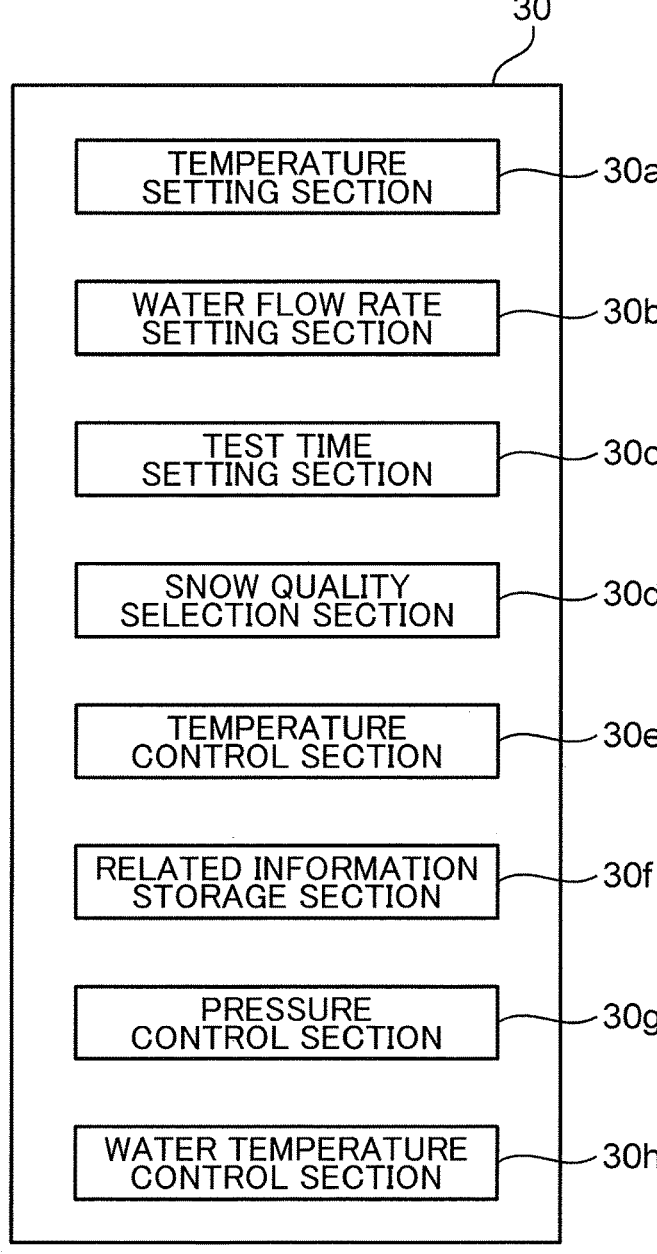
FIG. 9 is a diagram for describing functions of a controller in a snow environment test apparatus according to a third embodiment.

As illustrated in FIG. 9, in a third embodiment, the controller 30 also functions as the pressure control section 30*g* and the water temperature control section 30*h* in order to regulate the pressure of the air and the temperature of the water to be supplied to the injector 14 using the information stored in the related information storage section 30*f*. Note that the components identical to those in the first embodiment are denoted by the identical reference numerals, and the detailed description thereof will be omitted.

In the third embodiment, the controller 30 also functions as the pressure control section 30*g* as in the first embodiment, and the controller 30 also functions as the water temperature control section 30*h* as in the second embodiment.

The pressure control section 30$g$ is configured to control the pressure regulation valve 16$d$ to make the pressure of the air to be supplied to the injector 14 be a pressure that is derived by using the temperature in the test chamber 1 set in the temperature setting section 30$a$, the flow rate of the water set in the water flow rate setting section 30$b$, the snow quality set in the snow quality selection section 30$d$, and the information stored in the related information storage section 30$f$. That is, the pressure control section 30$g$ and the pressure regulation valve 16$d$ function as a pressure regulation section that regulates the pressure of the air to be supplied to the injector 14 to the pressure obtained by using the information stored in the related information storage section 30$f$.

The water temperature control section 30$h$ is configured to control the heating and cooling unit 18$c$ to make the temperature of the water to be supplied to the injector 14 be the temperature that is derived by using the temperature in the test chamber 1 set in the temperature setting section 30$a$, the flow rate of the water set in the water flow rate setting section 30$b$, the snow quality set in the snow quality selection section 30$d$, and the information stored in the related information storage section 30$f$. That is, the water temperature control section 30$h$ and the heating and cooling unit 18$c$ function as a water temperature regulation section that regulates the temperature of the water to be supplied to the injector 14 to the temperature obtained by using the information stored in the related information storage section 30$f$.

The related information storage section 30$f$ is a functional unit that stores information in which the temperature in the test chamber 1, the flow rate of the water to be supplied to the injector 14, the temperature of the water to be supplied to the injector 14, the pressure of the air to be supplied to the injector 14, and the snow quality are related with each other. The related information storage section 30$f$ may include, for example, a first map, a second map, and a third map. In the first map, the flow rate of the water, the water temperature, the air pressure, and the snow quality at the first test temperature (for example, −5° C.) are related with each other. In the second map, the flow rate of the water, the water temperature, the air pressure, and the snow quality at the second test temperature (for example, −10° C.) are related with each other. In the third map, the flow rate of the water, the water temperature, the air pressure, and the snow quality at the third test temperature (for example, −15° C.) are related with each other. That is, use of the information stored in the related information storage section 30$f$ makes it possible to derive which snow quality is obtained in the case of a certain water temperature, a certain flow rate of water, and a certain air pressure at each test temperature. In addition, in a case where certain snow quality is desired to be obtained at each test temperature, it is possible to derive what temperature (° C.) and how much air pressure (MPa) may be set under a certain flow rate of water. Note that dry snow, wet snow, sleet, and rain are stored as snow quality, but instead of or together with them, the degree of sleet or the water content may be stored. Further, the information stored in the related information storage section 30$f$ may be information expressed by a relational expression, information in the form of a list, or the like. In addition, the number of prepared test temperatures is not limited to three, and information in the case of one, two, or more test temperatures may be prepared.

Figure 10:
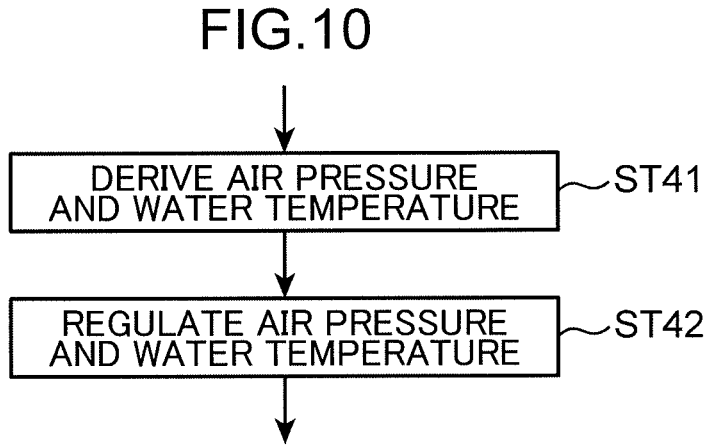
FIG. 10 is a flowchart for describing adjustment of an air pressure and a water temperature in a snow environment test method according to the third embodiment.

Here, as in the first embodiment, the example in the case where the test illustrated in FIG. 5 is performed will be described. In the third embodiment, as illustrated in FIG. 10, in each of the first to third tests, the pressure control section

30$g$ and the water temperature control section 30$h$ derive the pressure of the air to be supplied to the injector 14 and the temperature of the water to be supplied to the injector 14 using the temperature in the test chamber 1 set in the temperature setting section 30$a$, the flow rate of the water set in the water flow rate setting section 30$b$, the snow quality set in the snow quality selection section 30$d$, and the information stored in the related information storage section 30$f$ (step ST41). Then, the pressure control section 30$g$ controls the pressure regulation valve 16$d$ depending on the derived pressure, and the water temperature control section 30$h$ controls the heating and cooling unit 18$c$ depending on the derived temperature. As a result, during the test, the pressure of the air to be supplied to the injector 14 is regulated to the derived pressure, and the temperature of the water to be supplied to the injector 14 is regulated to the derived temperature (step ST42). At this time, the flow rate of water is regulated to the flow rate of the water set in the water flow rate setting section 30$b$.

Therefore, in the present embodiment, the temperature control section 30$e$ controls the air conditioner 12 to make the temperature in the test chamber 1 be the set temperature. The pressure regulation valve 16$d$ regulates the pressure of the air to be supplied to the injector 14 to the pressure obtained by using the snow quality selected by the snow quality selection section 30$d$ and the information stored in the related information storage section 30$f$. Further, the heating and cooling unit 18$c$ regulates the temperature of the water to be supplied to the injector 14 to the water temperature obtained by using the snow quality selected by the snow quality selection section 30$d$ and the information stored in the related information storage section 30$f$. As a result, air having the regulated pressure is supplied to the injector 14, and water having the regulated temperature and the flow rate set in the water flow rate setting section 30$b$ is supplied to the injector 14. Therefore, the snow environment of the snow quality selected by the snow quality selection section 30$d$ can be obtained, and the specimen can be exposed to such a snow environment.

Note that although descriptions of other configurations, operations, and effects are omitted, the descriptions of the first and second embodiments can be applied to the third embodiment.

Fourth Embodiment

Figure 11:
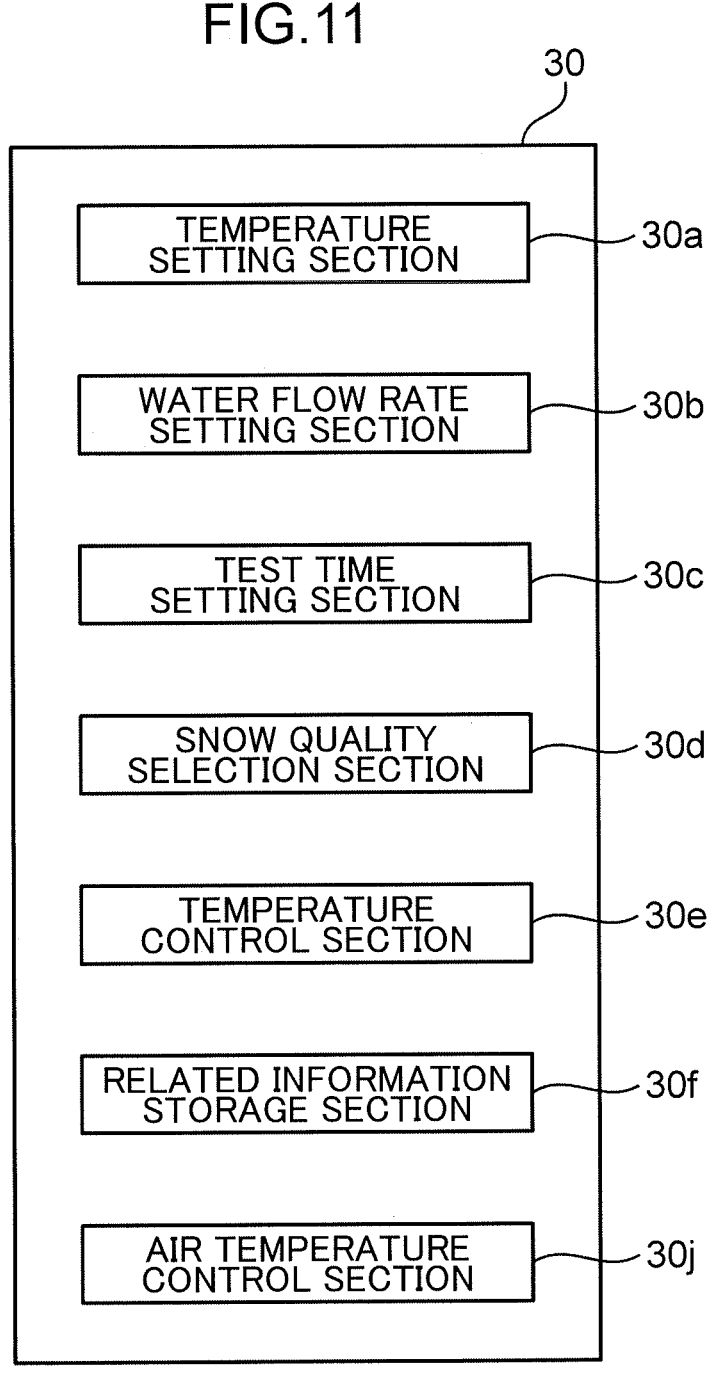
FIG. 11 is a diagram for describing functions of a controller in a snow environment test apparatus according to a fourth embodiment.

As illustrated in FIG. 11, in a fourth embodiment, the controller 30 also functions as an air temperature control section 30$j$ in order to regulate the temperature of the air to be supplied to the injector 14 using the information stored in the related information storage section 30$f$. Note that the components identical to those in the first embodiment are denoted by the identical reference numerals, and the detailed description thereof will be omitted.

In the fourth embodiment, unlike the first embodiment, the pressure control section 30$g$ is omitted. Therefore, although the pressure regulation valve 16$d$ is provided to the air pipe 16$a$, the pressure regulation valve 16$d$ may not be connected to the controller 30. The pressure regulation valve 16$d$ is provided to maintain the pressure of the air to be supplied to the injector 14 at a predetermined pressure. However, if the pressure of air to be discharged from the compressor 16$b$ is stable, the pressure regulation valve 16$d$ can be omitted.

Figures 12, 13:
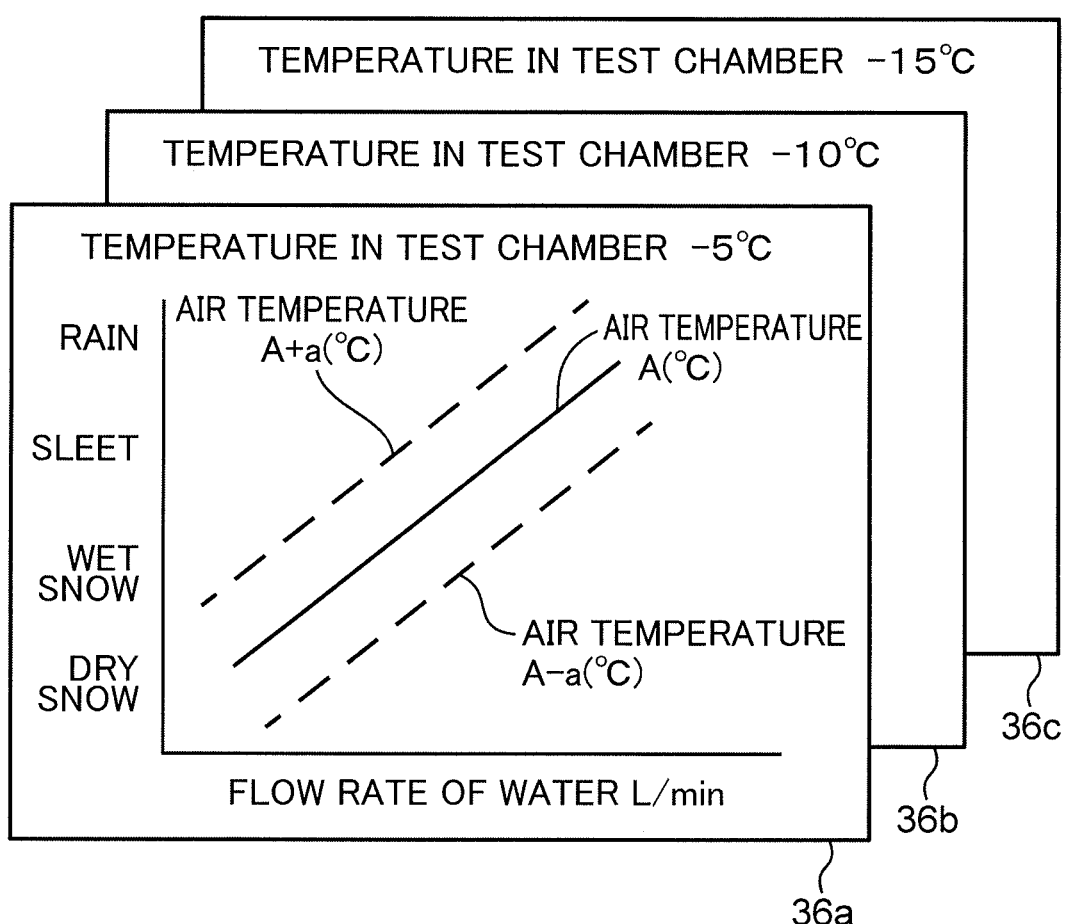
FIG. 12 is a diagram for describing information stored in a related information storage section.
FIG. 13 is a flowchart for describing adjustment of a water temperature in a snow environment test method according to the fourth embodiment.

The related information storage section 30$f$ is a functional unit that stores information in which the temperature in the test chamber 1, the flow rate of the water to be supplied to the injector 14, the temperature of the air to be supplied to the injector 14, and the snow quality are related with each other. As illustrated in FIG. 12, the related information storage section 30f may include, for example, a first map 36a, a second map 36b, and a third map 36c. In the first map 36a, the flow rate of water, the air temperature, and the snow quality at the first test temperature (for example, −5° C.) are related with each other. In the second map 36b, the flow rate of water, the air temperature, and the snow quality at the second test temperature (for example, −10° C.) are related with each other. In the third map 36c, the flow rate of water, the air temperature, and the snow quality at the third test temperature (for example, −15° C.) are related with each other. That is, use of the information stored in the related information storage section 30f makes it possible to derive which snow quality is obtained in the case of a certain air temperature and a certain flow rate of water at each test temperature. In addition, in a case where certain snow quality is desired to be obtained at each test temperature, it is possible to derive what air temperature (° C.) may be set under a certain flow rate of water. Note that dry snow, wet snow, sleet, and rain are stored as snow quality, but instead of or together with them, the degree of sleet or the water content may be stored. Further, the information stored in the related information storage section 30f may be information expressed by a relational expression, information in the form of a list, or the like. In addition, the number of prepared test temperatures is not limited to three, and information in the case of one, two, or more test temperatures may be prepared.

The air temperature control section 30j is configured to derive the temperature of the air to be supplied to the injector 14 using the temperature in the test chamber 1 set in the temperature setting section 30a, the flow rate of the water set in the water flow rate setting section 30b, the snow quality set in the snow quality selection section 30d, and the information stored in the related information storage section 30f. For example, in a case where the information illustrated in FIG. 12 is stored in the related information storage section 30f, the air temperature control section 30j refers to a map of a test temperature matching or similar to the temperature in the test chamber 1 set in the temperature setting section 30a. In the referred map, the air temperature is derived from the flow rate of the water set in the water flow rate setting section 30b and the snow quality set in the snow quality selection section 30d. The air temperature control section 30j is configured to control the heating and cooling unit 16e to make the temperature of the air to be supplied to the injector 14 be the temperature that is derived by using the temperature in the test chamber 1 set in the temperature setting section 30a, the flow rate of the water set in the water flow rate setting section 30b, the snow quality set in the snow quality selection section 30d, and the information stored in the related information storage section 30f. That is, the air temperature control section 30j and the heating and cooling unit 16e function as an air temperature regulation section that regulates the temperature of the air to be supplied to the injector 14 to the temperature obtained by using the information stored in the related information storage section 30f.

Here, as in the first embodiment, the example in the case where the test illustrated in FIG. 5 is performed will be described. In the fourth embodiment, as illustrated in FIG. 13, in each of the first to third tests, the air temperature control section 30j derives the temperature of the air to be supplied to the injector 14 using the temperature in the test chamber 1 set in the temperature setting section 30a, the flow rate of the water set in the water flow rate setting section 30b, the snow quality set in the snow quality selection section 30d, and the information stored in the related information storage section 30f (step ST41). In addition, the air temperature control section 30j controls the heating and cooling unit 16e depending on the derived temperature. As a result, during the test, the temperature of the air to be supplied to the injector 14 is regulated to be the derived temperature (step ST42). Specifically, the temperature of the air to be supplied to the injector 14 is regulated to decrease so that the snow quality is changed from sleet of the second test to wet snow of the third test. At this time, the flow rate of water is adjusted to the flow rate of the water set in the water flow rate setting section 30b. On the other hand, the air to be supplied to the injector 14 is regulated by the pressure regulation valve 16d to be a predetermined pressure. That is, unlike the first embodiment, the fourth embodiment does not include the step of deriving the air pressure using the information stored in the related information storage section 30f (steps ST17, ST20, and ST23), and the step of regulating the air pressure using the information stored in the related information storage section 30f (ST18, ST21, and ST24).

Therefore, in the present embodiment, the temperature control section 30e controls the air conditioner 12 to make the temperature in the test chamber 1 be the set temperature. The heating and cooling unit 16e regulates the temperature of the air to be supplied to the injector 14 to the temperature obtained by using the snow quality selected by the snow quality selection section 30d and the information stored in the related information storage section 30f. As a result, water having a predetermined temperature and the flow rate set in the water flow rate setting section 30b, and air having a predetermined pressure and the regulated temperature are supplied to the injector 14. Therefore, the snow environment of the snow quality selected by the snow quality selection section 30d can be obtained, and the specimen can be exposed to such a snow environment.

Note that although descriptions of other configurations, operations, and effects are omitted, the descriptions of the first to third embodiments can be applied to the fourth embodiment.

Fifth Embodiment

Figure 14:
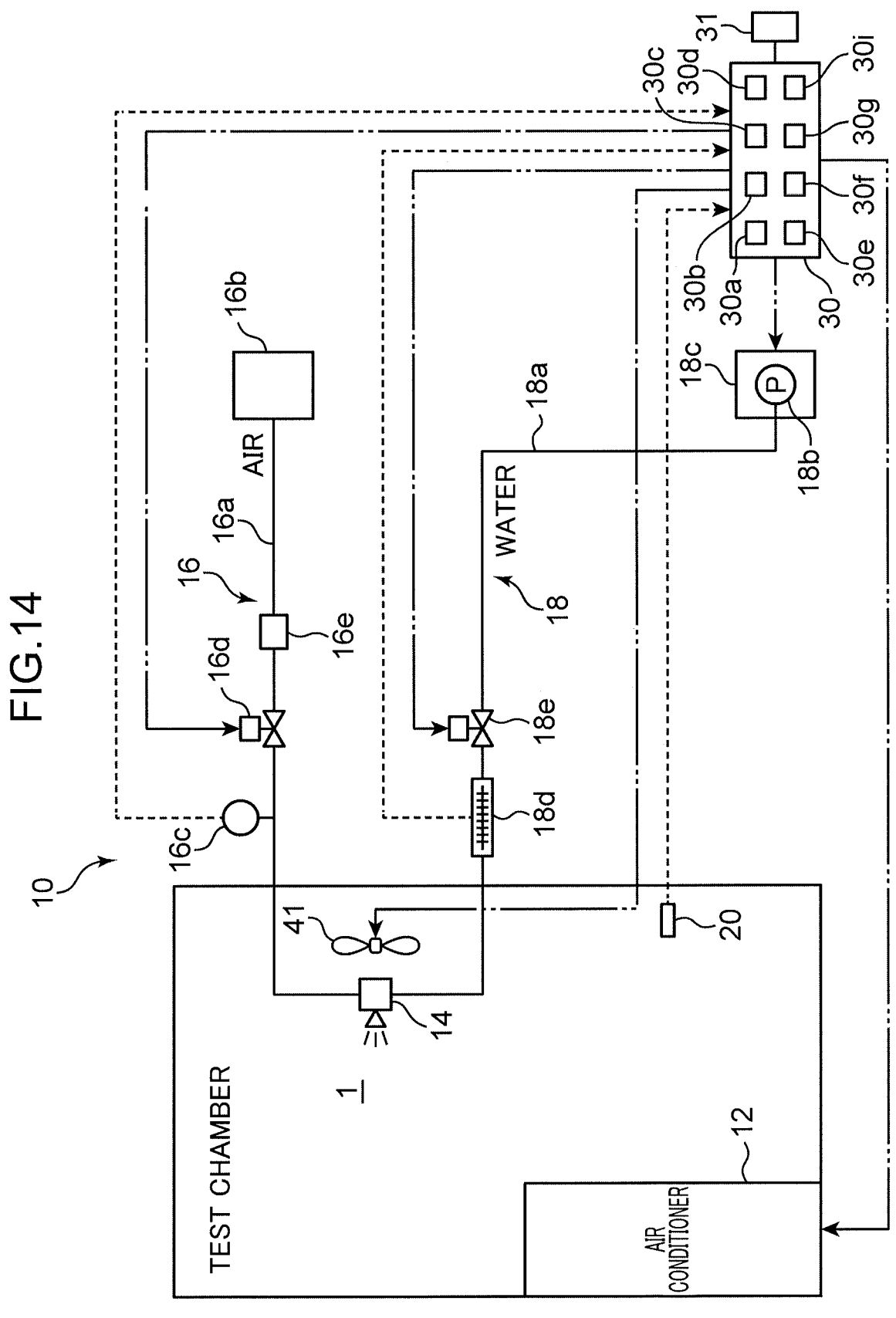
FIG. 14 is a diagram schematically illustrating a snow environment test apparatus according to a fifth embodiment.

FIG. 14 illustrates a fifth embodiment. Note that the components identical to those in the first to third embodiments are denoted by the identical reference numerals, and the detailed description thereof will be omitted.

In the fifth embodiment, a blower 41 configured to generate an air flow in the test chamber 1 is provided, and the controller 30 also functions as an air blowing control section 30i. Note that although FIG. 14 illustrates a case where the controller 30 also functions as the pressure control section 30g, instead of or in addition to this, the controller 30 may also function as the water temperature control section 30h.

The air blowing control section 30i is a functional unit for controlling the blower 41, and can increase or decrease the rotation speed of the blower 41 based on a signal input through the input device 31. For example, when the quality of snow adhering to the specimen is drier than expected, the tester performs an operation for increasing the rotation speed of the blower 41 through the input device 31. As a result, the fine water droplets injected from the injector 14 reach the specimen before being completely frozen. Therefore, the water content of snow adhering to the specimen can be increased. For example, when the amount of snow adhering to the specimen is smaller than expected, the tester increases the rotation speed of the blower 41 through the input device 31. As a result, the water content of snow reaching the specimen is slightly increased, and thus the snow easily adheres to the specimen.

Therefore, in the present embodiment, since the flow velocity of airflow generated in the test chamber 1 can be changed, the time until the water droplets injected from the injector 14 reach the specimen can be changed. Therefore, the snow quality at the time of reaching the specimen can be further regulated by the flow velocity of air. Therefore, it is possible to change the amount of snow adhering to the specimen and the quality of snow adhering to the specimen.

Note that although descriptions of other configurations, operations, and effects are omitted, the descriptions of the first to fourth embodiments can be applied to the fifth embodiment.

Here, the above-described embodiments will be outlined.

(1) A snow environment test apparatus according to the embodiment is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a water supply section configured to supply water having a predetermined temperature and the flow rate set by the water flow rate setting section to the injector, a snow quality selection section configured to select snow quality, a related information storage section storing information in which a temperature in the test chamber, a flow rate of water to be supplied to the injector, a pressure of air to be supplied to the injector, and a snow quality are related with each other, and a pressure regulation section configured to regulate the pressure of the air to be supplied to the injector to a pressure obtained by using the information stored in the related information storage section so that the snow quality selected by the snow quality selection section is obtained.

In the snow environment test apparatus, the temperature control section controls the air conditioner to make the temperature in the test chamber be the set temperature. The pressure regulation section regulates the pressure of the air to be supplied to the injector to the pressure obtained by using the snow quality selected by the snow quality selection section and the information stored in the related information storage section. As a result, air having the regulated pressure is supplied to the injector, and water having the flow rate set by the water flow rate setting section and a predetermined temperature is supplied to the injector. Therefore, the snow environment of the snow quality selected by the snow quality selection section can be obtained, and a specimen can be exposed to such a snow environment.

That is, the snow quality (for example, any one of dry snow, wet snow, and sleet) changes depending on the temperature in the test chamber, the flow rate of the water to be supplied to the injector including the two-fluid nozzle, and the pressure of the air to be supplied to the injector. For this reason, it is not clear whether desired snow quality can be obtained unless snow is actually cause to fall. On the other hand, the snow environment test apparatus includes the related information storage section that stores information in which the three conditions and the snow quality are related with each other. In this apparatus, the pressure of the air to be supplied to the injector is regulated by using this information depending on the set test chamber temperature and the set water flow rate at a predetermined temperature. Thus, a snow environment of desired snow quality can be obtained. Therefore, preparation, and time and effort for obtaining desired snow quality can be reduced. Note that the information stored in the related information storage section can be acquired by a preliminary test to cause snow to actually fall after regulating of these three conditions and check the snow quality.

(2) A snow environment test apparatus according to the embodiment is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a water supply section configured to supply water having the flow rate set by the water flow rate setting section, an air supply section configured to supply air having a predetermined pressure to the injector, a snow quality selection section configured to select snow quality, a related information storage section storing information in which a temperature in the test chamber, a flow rate of water to be supplied to the injector, a temperature of water to be supplied to the injector, and a snow quality are related with each other, and a water temperature regulation section configured to regulate the temperature of the water to be supplied to the injector to a temperature obtained by using the information stored in the related information storage section so that the snow quality selected by the snow quality selection section is obtained.

In the snow environment test apparatus, the temperature control section controls the air conditioner to make the temperature in the test chamber be the set temperature. The water temperature regulation section regulates the temperature of the water to be supplied to the injector to a water temperature obtained by using the snow quality selected by the snow quality selection section and the information stored in the related information storage section. As a result, water having the regulated temperature and the flow rate set by the water flow rate setting section, and air having a predetermined pressure are supplied to the injector. Therefore, the snow environment of the snow quality selected by the snow quality selection section can be obtained, and a specimen can be exposed to such a snow environment.

That is, since the snow quality (for example, any one of dry snow, wet snow, and sleet) changes depending on the temperature in the test chamber, the flow rate and temperature of the water to be supplied to the injector including the two-fluid nozzle, it is not clear whether desired snow quality can be obtained unless snow is caused to actually fall. On the contrary, the snow environment test apparatus includes the related information storage section that stores information in which the three conditions and the snow quality are related with each other. In this apparatus, the temperature of the water to be supplied to the injector is regulated by using this information depending on the set test chamber temperature, the predetermined air pressure, and the set water flow rate. Thus, a snow environment of desired snow quality can be obtained. Therefore, preparation, and time and effort for obtaining desired snow quality can be reduced. Note that the information stored in the related information storage section can be acquired by a preliminary test to cause snow to actually fall after regulating of these three conditions and check the snow quality.

(3) Further, a snow environment test apparatus according to the embodiment is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set by the temperature setting section, a water flow rate setting section configured to set a flow rate of water to be supplied to the injector, a snow quality selection section configured to select snow quality, a related information storage section storing information in which a temperature in the test chamber, a flow rate of water to be supplied to the injector, a temperature of water to be supplied to the injector, a pressure of air to be supplied to the injector, and a snow quality are related with each other, a pressure regulation section configured to regulate the pressure of the air to be supplied to the injector to a pressure obtained by using the information stored in the related information storage section so that the snow quality selected by the snow quality setting section is obtained, and a water temperature regulation section configured to regulate the temperature of the water to be supplied to the injector to a temperature obtained by using the information stored in the related information storage section so that the snow quality selected by the snow quality selection section is obtained.

In the snow environment test apparatus, the temperature control section controls the air conditioner to make the temperature in the test chamber be the set temperature. The pressure regulation section regulates the pressure of the air to be supplied to the injector to the pressure obtained by using the snow quality selected by the snow quality selection section and the information stored in the related information storage section. The water temperature regulation section regulates the temperature of the water to be supplied to the injector to a water temperature obtained by using the snow quality selected by the snow quality selection section and the information stored in the related information storage section. As a result, air having the regulated pressure is supplied to the injector, and water having the regulated temperature and the flow rate set in the water flow rate setting section is supplied to the injector. Therefore, the snow environment of the snow quality selected by the snow quality selection section can be obtained, and the specimen can be exposed to such a snow environment.

That is, since the snow quality (for example, any one of dry snow, wet snow, and sleet) changes depending on the temperature in the test chamber, the flow rate of water to be supplied to the injector including the two-fluid nozzle, the temperature of the water to be supplied to the injector, and the pressure of the air to be supplied to the injector, it is not clear whether desired snow quality can be obtained unless snow is caused to actually fall. On the contrary, the snow environment test apparatus includes the related information storage section that stores information in which the four conditions and the snow quality are related with each other. In this apparatus, the pressure of the air to be supplied to the injector and the temperature of the water to be supplied to the injector are regulated by using this information depending on the set test chamber temperature and the set water flow rate. Thus, a snow environment of desired snow quality can be obtained. Therefore, preparation, and time and effort for obtaining desired snow quality can be reduced. Note that the information stored in the related information storage section can be acquired by a preliminary test to cause snow to actually fall after regulating of these four conditions and check the snow quality.

(4) A snow environment test apparatus according to the embodiment is a snow environment test apparatus for creating a snow environment in a test chamber, the apparatus including an injector configured by a two-fluid nozzle and configured to inject water and air, a temperature setting section configured to set a temperature in the test chamber, an air conditioner configured to cool an inside of the test chamber, a temperature control section configured to control the air conditioner to make the temperature in the test chamber be the temperature set in the temperature setting section, a water flow rate setting section configured to set a flow rate of water to be supplied to the injector, a water supply section configured to supply water having the flow rate set in the water flow rate setting section, an air supply section configured to supply air having a predetermined pressure to the injector, a snow quality selection section configured to select snow quality, a related information storage section storing information in which a temperature in the test chamber, a flow rate of water to be supplied to the injector, a temperature of air to be supplied to the injector, and a snow quality are related with each other, and an air temperature regulation section configured to regulate the temperature of the air to be supplied to the injector to a temperature obtained by using the information stored in the related information storage section so that the snow quality selected by the snow quality selection section is obtained.

In the snow environment test apparatus, the temperature control section controls the air conditioner to make the temperature in the test chamber be the set temperature. The air temperature regulation section regulates the temperature of the air to be supplied to the injector to the temperature obtained by using the snow quality selected by the snow quality selection section and the information stored in the related information storage section. As a result, water having the flow rate set in the water flow rate setting section, and air having the regulated pressure are supplied to the injector. Therefore, the snow environment of the snow quality selected by the snow quality selection section can be obtained, and a specimen can be exposed to such a snow environment.

That is, since the snow quality (for example, any one of dry snow, wet snow, and sleet) changes depending on the temperature in the test chamber, the flow rate of water to be supplied to the injector including the two-fluid nozzle, and the temperature of the air, it is not clear whether desired snow quality can be obtained unless snow is caused to actually fall. On the contrary, the snow environment test apparatus includes the related information storage section that stores information in which the three conditions and the snow quality are related with each other. In this apparatus, the temperature of the air to be supplied to the injector is regulated by using this information depending on the set test chamber temperature, the predetermined air pressure, and the set water flow rate. Thus, a snow environment of desired snow quality can be obtained. Therefore, preparation, and time and effort for obtaining desired snow quality can be reduced. Note that the information stored in the related information storage section can be acquired by a preliminary test to cause snow to actually fall after regulating of these three conditions and check the snow quality.

(5) The snow environment test apparatus may include a blower that generates an airflow in the test chamber, and an air blowing control section that controls the blower.

In this aspect, since the flow velocity of airflow generated in the test chamber can be changed, the time until water droplets injected from the injector reach a specimen can be changed. Therefore, the snow quality at the time of reaching the specimen can be further regulated by the flow velocity of air. Therefore, it is possible to change the amount of snow adhering to the specimen and the quality of snow adhering to the specimen.

(6) A snow environment test method according to the embodiment is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a pressure of air to be supplied to the injector providing the selected snow quality using information in which a temperature in the test chamber, a flow rate of water to be supplied to the injector, a pressure of air to be supplied to the injector, and a snow quality are related with each other, the information being stored in a related information storage section; supplying water having a predetermined temperature and the flow rate set by the water flow rate setting section to the injector; supplying air having the derived pressure to the injector; and injecting the water and the air from the injector.

With the snow environment test method, the snow quality is selected by the snow quality selection section, the flow rate of the water to be supplied to the injector is set, and the air conditioner is controlled to make the temperature in the test chamber be the set temperature. Air having the pressure obtained by using the information stored in the related information storage section is supplied to the injector, and water having the predetermined temperature and the flow rate set by the water flow rate setting section is supplied to the injector. Therefore, the snow environment of the snow quality selected by the snow quality selection section can be obtained, and a specimen can be exposed to such a snow environment.

(7) A snow environment test method according to the embodiment is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a temperature of the water to be supplied to the injector providing the selected snow quality using information in which a temperature in the test chamber, a flow rate of water to be supplied to the injector, a temperature of water to be supplied to the injector, and a snow quality are related with each other, the information being stored in a related information storage section; supplying water, having the derived temperature and the flow rate set by the water flow rate setting section, to the injector; supplying air having a predetermined pressure to the injector; and injecting the water and the air from the injector.

With the snow environment test method, the snow quality is selected by the snow quality selection section, the flow rate of the water to be supplied to the injector is set, and the air conditioner is controlled to make the temperature in the test chamber be the set temperature. As a result, water having the temperature obtained by using the information stored in the related information storage section and the flow rate set in the water flow rate setting section is supplied to the injector, and air having the predetermined pressure is supplied to the injector. Therefore, the snow environment of the snow quality selected by the snow quality selection section can be obtained, and a specimen can be exposed to such a snow environment.

(8) A snow environment test method according to the embodiment is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a pressure of air to be supplied to the injector providing the selected snow quality and deriving a temperature of the water to be supplied to the injector providing the selected snow quality, using information in which a temperature in the test chamber, a flow rate of water to be supplied to the injector, a temperature of water to be supplied to the injector, a pressure of air to be supplied to the injector, and a snow quality are related with each other, the information being stored in a related information storage section; supplying water having the derived temperature and the flow rate set by the water flow rate setting section to the injector; supplying air having the derived pressure to the injector; and injecting the water and the air from the injector.

With the snow environment test method, the snow quality is selected by the snow quality selection section, the flow rate of water to be supplied to the injector is set, and the air conditioner is controlled to make the temperature in the test chamber be the set temperature. As a result, air having the pressure obtained by using the information stored in the related information storage section is supplied to the injector, and water having the temperature obtained by using the information stored in the related information storage section and the flow rate set by the water flow rate setting section is supplied to the injector. Therefore, the snow environment of the snow quality selected by the snow quality selection section can be obtained, and a specimen can be exposed to such a snow environment.

(9) A snow environment test method according to the embodiment is a snow environment test method for creating a snow environment in a test chamber, the method including setting a temperature in the test chamber; selecting snow quality by a snow quality selection section; setting a flow rate of water to be supplied to an injector including a two-fluid nozzle by a water flow rate setting section; controlling an air conditioner to make the temperature in the test chamber be the set temperature; deriving a temperature of air to be supplied to the injector providing the selected snow quality using information in which a temperature in the test chamber, a flow rate of water to be supplied to the injector, a temperature of air to be supplied to the injector, and a snow quality are related with each other, the information being stored in a related information storage section; supplying water having a predetermined temperature and the flow rate set by the water flow rate setting section to the injector; supplying air having a predetermined pressure and the derived temperature to the injector; and injecting the water and the air from the injector.

With the snow environment test method, the snow quality is selected by the snow quality selection section, the flow rate of water to be supplied to the injector is set, and the air conditioner is controlled to make the temperature in the test chamber be the set temperature. As a result, air having the temperature obtained by using the information stored in the related information storage section and the predetermined pressure is supplied to the injector, and water having the flow rate set in the water flow rate setting section is supplied to the injector. Therefore, the snow environment of the snow quality selected by the snow quality selection section can be obtained, and a specimen can be exposed to such a snow environment.

As described above, time and effort for reproducing a snow environment where snow having desired snow quality is caused to fall can be reduced.

This application is based on Japanese Patent application No. 2022-137110 filed in Japan Patent Office on Aug. 30, 2022, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A snow environment test apparatus for creating a snow environment in a test chamber, the apparatus comprising:
an injector configured by a two-fluid nozzle and configured to inject water and air;
a temperature setting section configured to set a temperature in the test chamber;
an air conditioner configured to cool an inside of the test chamber;
a temperature controller configured to control the air conditioner to make the temperature in the test chamber be the temperature set by the temperature setting section;
a water flow rate setting section configured to set a flow rate of water to be supplied to the injector;
a water supplier configured to supply water having a predetermined temperature and the flow rate set by the water flow rate setting section to the injector,
a pressure regulator configured to regulate a pressure of air to be supplied to the injector;
a snow quality selector configured to select one of dry snow, wet snow, or sleet as a snow quality; and a related information storage section storing information in which a temperature in the test chamber, a flow rate of water to be supplied to the injector, a pressure of air to be supplied to the injector, and a snow quality including dry snow, wet snow, and sleet are related with each other, wherein
the pressure regulator includes a pressure controller configured to derive the pressure of the air to be supplied to the injector by using the temperature in the test chamber set by the temperature setting section, the flow rate of the water set by the water flow rate setting section, the snow quality selected by the snow quality selector, and the information stored in the related information storage section, and
the pressure regulator is configured to make the pressure of the air to be supplied to the injector become the pressure of the air derived by the pressure controller.

2. The snow environment test apparatus according to claim 1, further comprising:
a blower for generating an airflow in the test chamber; and
an air blowing controller for controlling the blower.

3. A snow environment test apparatus for creating a snow environment in a test chamber, the apparatus comprising:
an injector configured by a two-fluid nozzle and configured to inject water and air;
a temperature setting section configured to set a temperature in the test chamber;
an air conditioner configured to cool an inside of the test chamber;
a pressure regulator configured to regulate a pressure of air to be supplied to the injector;
a water temperature regulator configured to adjust a temperature of water to be supplied to the injector;
a temperature controller configured to control the air conditioner to make the temperature in the test chamber be the temperature set by the temperature setting section;
a water flow rate setting section configured to set a flow rate of the water to be supplied to the injector;
a snow quality selector configured to select one of dry snow, wet snow, or sleet as a snow quality;
a related information storage section storing information in which a temperature in the test chamber, a flow rate of water to be supplied to the injector, a temperature of water to be supplied to the injector, a pressure of air to be supplied to the injector, and a snow quality including dry snow, wet snow, and sleet are related with each other; wherein
the pressure regulator includes a pressure controller configured to derive the pressure of the air to be supplied to the injector using the temperature in the test chamber set by the temperature setting section, the flow rate of the water set by the water flow rate setting section, the snow quality selected by the snow quality selector, and the information stored in the related information storage section,
the pressure regulator is configured to make the pressure of the air to be supplied to the injector become the pressure of the air derived by the pressure controller;
the water temperature regulator includes a water temperature controller configured to derive the temperature of the water to be supplied to the injector using the temperature in the test chamber set by the temperature setting section, the flow rate of the water set by the water flow rate setting section, the snow quality selected by the snow quality selector, and the information stored in the related information storage section, and the water temperature regulator is configured to make the temperature of the water to be supplied to the injector become the temperature derived by the water temperature controller.

4. The snow environment test apparatus according to claim 3, further comprising:

a blower for generating an airflow in the test chamber; and an air blowing controller for controlling the blower.

5. A snow environment test method for creating a snow environment in a test chamber, the method comprising:

setting a temperature in the test chamber;

selecting one of dry snow, wet snow, or sleet as a snow quality by a snow quality selection section;

setting a flow rate of water to be supplied to an injector including a two-fluid nozzle by a water flow rate setting section;

controlling an air conditioner to make the temperature in the test chamber be the set temperature;

deriving a pressure of air to be supplied to the injector using the set temperature in the test chamber, the flow rate of the water set by the water flow rate setting section, the snow quality selected by the snow quality selection section, and information in which a temperature in the test chamber, a flow rate of water to be supplied to the injector, a pressure of air to be supplied to the injector, and a snow quality including dry snow, wet snow, and sleet are related with each other, the information being stored in a related information storage section;

supplying water having a predetermined temperature and the flow rate set by the water flow rate setting section to the injector;

supplying air having the derived pressure to the injector; and injecting the water and the air from the injector.

6. A snow environment test method for creating a snow environment in a test chamber, the method comprising:

setting a temperature in the test chamber;

selecting one of dry snow, wet snow, or sleet as a snow quality by a snow quality selection section;

setting a flow rate of water to be supplied to an injector including a two-fluid nozzle by a water flow rate setting section;

controlling an air conditioner to make the temperature in the test chamber be the set temperature;

deriving a pressure of air to be supplied to the injector and a temperature of the water to be supplied to the injector using the set temperature in the test chamber, the snow quality selected by the snow quality selection section, the flow rate of the water set by the water flow rate setting section, and information in which a temperature in the test chamber, a flow rate of water to be supplied to the injector, a temperature of water to be supplied to the injector, a pressure of air to be supplied to the injector, and the snow quality including dry snow, wet snow, and sleet are related with each other, the information being stored in a related information storage section;

supplying water having the derived temperature and the flow rate set by the water flow rate setting section to the injector;

supplying air having the derived pressure to the injector; and injecting the water and the air from the injector.

*     *     *     *     *